United States Patent
Short et al.

(12) 
(10) Patent No.: US 6,444,426 B1
(45) Date of Patent: *Sep. 3, 2002

(54) PRODUCTION AND USE OF NORMALIZED DNA LIBRARIES

(75) Inventors: Jay M. Short, Rancho Sante Fe; Eric J. Mathur, Carlsbad, both of CA (US)

(73) Assignee: Diversa Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/437,905

(22) Filed: Nov. 9, 1999

Related U.S. Application Data

(63) Continuation of application No. 09/034,724, filed on Mar. 4, 1998, now Pat. No. 6,001,574, which is a continuation-in-part of application No. 08/665,565, filed on Jun. 18, 1996, now Pat. No. 5,763,239.

(51) Int. Cl.$^7$ ............................. C12Q 1/70; C12Q 1/68; C12D 19/34
(52) U.S. Cl. ......................... 435/6; 435/91.2; 435/440; 536/25.4; 536/25.42
(58) Field of Search ........................... 435/91.2, 6, 440; 536/25.4, 25.42

(56) References Cited

U.S. PATENT DOCUMENTS 5,763,239 A    6/1998   Short et al.

FOREIGN PATENT DOCUMENTS

| WO | WO9508647 | 3/1995 |
| WO | WO 97/48717 | 12/1997 |
| WO | WO 99/15702 | 4/1999 |
| WO | WO 99/45154 | 9/1999 |

OTHER PUBLICATIONS

Jeffery L. Stein, et al., Characterization of Uncultivated Prokaryotes: Isolation and Analysis of a 40–Kilobase–Pair Genome Fragment from a Planktonic Marine Archaeon, Feb. 1996, Journal of Bacteriology, pp. 591–599, vol. 178, No. 3.*

Patanjali et al., "Construction of a Uniform–Abundance (Normalized) cDNA Library," *Proceedings of the National Academy of Sciences of USA;* 88(5):1943–1947 (Mar. 1, 1991).

Soares et al., "Construction and characterization of a normalized cDNA library," *Proceedings National Academy of Sciences* 91:9228–9232 (Sep. 1994).

Stein et al., "Characterization of uncultivated prokaryotes: isolation and analysis of a 40–kilobase–pair genome fragment from a planktonic marine archaeon," *Journal of Bacteriology* 178(3):591–599.

Simoens et al., "Isolation of genes expressed in specific tissues of *Arabidopsis thaliana* by differential screening of a genomic library," *Gene,* 67:1–11 (1988).

Simoens et al., Isolation of Genes Expressed in Specific Tissues of *Arabidopsis thaliana* by Differential Screening of a Genomic Library, Gene 1998, vol. 6, pp. 1–11.

* cited by examiner

Primary Examiner—Sean McGarry
(74) *Attorney, Agent, or Firm*—Gray, Cary, Ware & Freidenrich LLP; Lisa A. Haile

(57) ABSTRACT

Disclosed is a process for forming a normalized genomic DNA library from an environmental sample by (a) isolating a genomic DNA population from the environmental sample; (b) at least one of (i) amplifying the copy number of the DNA population so isolated and (ii) recovering a fraction of the isolated genomic DNA having a desired characteristic; and (c) normalizing the representation of various DNAs within the genomic DNA population so as to form a normalized library of genomic DNA from the environmental sample. Also disclosed is a normalized genomic DNA library formed from an environmental sample by the process.

19 Claims, 1 Drawing Sheet

US 6,444,426 B1

PRODUCTION AND USE OF NORMALIZED DNA LIBRARIES

This application con't of 35 U.S.C. §120 to U.S. patent application Ser. No. 09/034,724; filed on Mar. 4, 1998, now U.S. Pat. No. 6,001,574, which is a continuation-in-part of U.S. application Ser. No. 08/665,565, filed Jun. 18, 1996, now issued as U.S. Pat. No. 5,763,239, the contents of which are both incorporated by reference in their entirety herein.

FIELD OF THE INVENTION

The present invention relates to the field of production and screening of gene libraries, and more particularly to the generation and screening of normalized genomic DNA libraries from mixed populations of microbes and/or other organisms.

BACKGROUND OF THE INVENTION

There has been increasing demand in the research reagent, diagnostic reagent and chemical process industries for protein-based catalysts possessing novel capabilities. At present, this need is largely addressed using enzymes purified from a variety of cultivated bacteria or fungi. However, because less than 1% of naturally occurring microbes can be grown in pure culture (Amann, 1995), alternative techniques must be developed to exploit the full breadth of microbial diversity for potentially valuable new products.

Virtually all of the commercial enzymes now in use have come from cultured organisms. Most of these organisms are bacteria or fungi. Amann et al. (Amann, 1995) have estimated cultivated microorganisms in the environment as follows:

| Habitat | Culturability (%) |
| --- | --- |
| Seawater | 0.001–0.1 |
| Freshwater | 0.25 |
| Mesotrophic lake | 0.01–1.0 |
| Unpolluted esturine waters | 0.1–3.0 |
| Activated sludge | 1.0–15.0 |
| Sediments | 0.25 |
| Soil | 0.3 |

These data were determined from published information regarding the number of cultivated microorganisms derived from the various habitats indicated.

Other studies have also demonstrated that cultivated organisms comprise only a small fraction of the biomass present in the environment. For example, one group of workers recently reported the collection of water and sediment samples from the "Obsidian Pool" in Yellowstone National Park (Barns, 1994) where they found cells hybridizing to archaea-specific probes in 55 % of 75 enrichment cultures. Amplification and cloning of 16S rRNA encoding sequences revealed mostly unique sequences with little or no representation of the organisms which had previously been cultured from this pool, suggesting the existence of substantial diversity of archaea with so far unknown morphological, physiological and biochemical features. Another group performed similar studies on the cyanobacterial mat of Octopus Spring in Yellowstone Park and came to the same conclusion; namely, tremendous uncultured diversity exists (Ward, 1990). Giovannoni et al. (1990) and Torsvik et al. (1990a) have reported similar results using bacterioplankton collected in the Sargasso Sea and in soil samples, respectively. These results indicate that the exclusive use of cultured organisms in screening for useful enzymatic or other bioactivities severely limits the sampling of the potential diversity in existence.

Screening of gene libraries from cultured samples has already proven valuable. It has recently been made clear, however, that the use of only cultured organisms for library generation limits access to the diversity of nature. The uncultivated organisms present in the environment, and/or enzymes or other bioactivities derived thereof, may be useful in industrial processes. The cultivation of each organism represented in any given environmental sample would require significant time and effort. It has been estimated that in a rich sample of soil, more than 10,000 different species can be present. It is apparent that attempting to individually cultivate each of these species would be a cumbersome task. Therefore, novel methods of efficiently accessing the diversity present in the environment are highly desirable.

SUMMARY OF THE INVENTION

The present invention addresses this need by providing methods to isolate the DNA from a variety of sources, including isolated organisms, consortias of microorganisms, primary enrichments, and environmental samples, to make libraries which have been "normalized" in their representation of the genome populations in the original samples, and to screen these libraries for enzyme and other bioactivities.

The present invention represents a novel, recombinant approach to generate and screen DNA libraries constructed from mixed microbial populations of cultivated or, preferably, uncultivated (or "environmental") samples. In accordance with the present invention, libraries with equivalent representation of genomes from microbes that can differ vastly in abundance in natural populations are generated and screened. This "normalization" approach reduces the redundancy of clones from abundant species and increases the representation of clones from rare species. These normalized libraries allow for greater screening efficiency resulting in the isolation of genes encoding novel biological catalysts.

Screening of mixed populations of organisms has been made a rational approach because of the availability of techniques described herein, whereas previously attempts at screening of mixed population were not feasible and were avoided because of the cumbersome procedures required.

Thus, in one aspect the invention provides a process for forming a normalized genomic DNA library from an environmental sample by (a) isolating a genomic DNA population from the environmental sample; (b) at least one of (i) amplifying the copy number of the DNA population so isolated and (ii) recovering a fraction of the isolated genomic DNA having a desired characteristic; and (c) normalizing the representation of various DNAs within the genomic DNA population so as to form a normalized library of genomic DNA from the environmental sample.

In one preferred embodiment of this aspect, the process comprises the step of recovering a fraction of the isolated genomic DNA having a desired characteristic.

In another preferred embodiment of this aspect, the process comprises the step of amplifying the copy number of the DNA population so isolated.

In another preferred embodiment of this aspect, the step of amplifying the genomic DNA precedes the normalizing step. In an alternate preferred embodiment of this aspect, the step of normalizing the genomic DNA precedes the amplifying step.

In another preferred embodiment of this aspect, the process comprises both the steps of (i) amplifying the copy number of the DNA population so isolated and (ii) recovering a fraction of the isolated genomic DNA having a desired characteristic.

Another aspect of the invention provides a normalized genomic DNA library formed from an environmental sample by a process comprising the steps of (a) isolating a genomic DNA population from the environmental sample; (b) at least one of (i) amplifying the copy number of the DNA population so isolated and (ii) recovering a fraction of the isolated genomic DNA having a desired characteristic; and (c) normalizing the representation of various DNAs within the genomic DNA population so as to form a normalized library of genomic DNA from the environmental sample. The various preferred embodiments described with respect to the above method aspect of the invention are likewise applicable with regard to this aspect of the invention.

The invention also provides a process for forming a normalized genomic DNA library from an environmental sample by (a) isolating a genomic DNA population from the environmental sample; (b) at least one of (i) amplifying the copy number of the DNA population so isolated and (ii) recovering a fraction of the isolated genomic DNA having a desired characteristic; and (c) normalizing the representation of various DNAs within the genomic DNA population so as to form a normalized library of genomic DNA from the environmental sample.

Another aspect of the invention provides a normalized genomic DNA library formed from an environmental sample by a process comprising the steps of (a) isolating a genomic DNA population from the environmental sample; (b) at least one of (i) amplifying the copy number of the DNA population so isolated and (ii) recovering a fraction of the isolated genomic DNA having a desired characteristic; and (c) normalizing the representation of various DNAs within the genomic DNA population so as to form a normalized library of genomic DNA from the environmental sample. The various preferred embodiments described with respect to the above method aspect of the invention are likewise applicable with regard to this aspect of the invention.

DETAILED DESCRIPTION OF THE INVENTION

DNA Isolation

Figure 1:
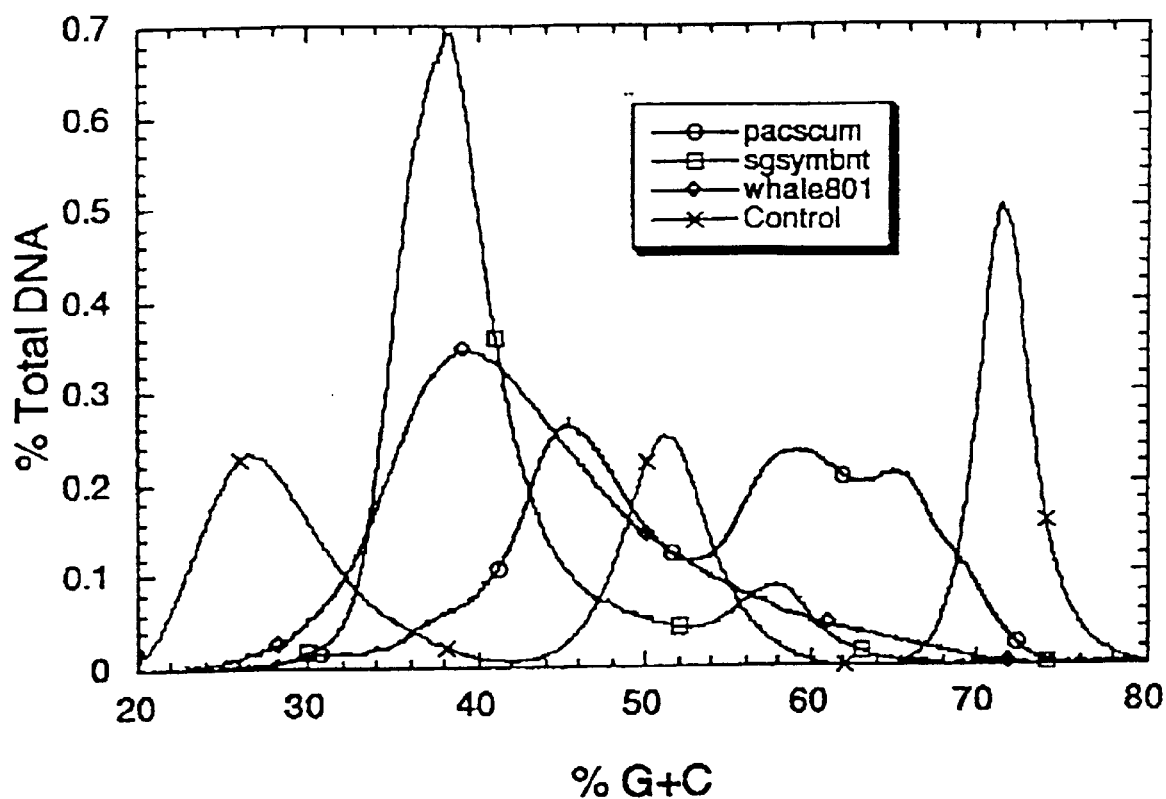
FIG. 1 is a graph showing the percent of total DNA content represented by G+C in the various genomic DNA isolates tested as described in Example 2.

An important step in the generation of a normalized DNA library from an environmental sample is the preparation of nucleic acid from the sample. DNA can be isolated from samples using various techniques well known in the art (*Nucleic Acids in the Environment Methods & Applications,* J. T. Trevors, D. D. van Elsas, Springer Laboratory, 1995). Preferably, DNA obtained will be of large size and free of enzyme inhibitors and other contaminants. DNA can be isolated directly from the environmental sample (direct lysis) or cells may be harvested from the sample prior to DNA recovery (cell separation). Direct lysis procedures have several advantages over protocols based on cell separation. The direct lysis technique provides more DNA with a generally higher representation of the microbial community, however, it is sometimes smaller in size and more likely to contain enzyme inhibitors than DNA recovered using the cell separation technique. Very useful direct lysis techniques have recently been described which provide DNA of high molecular weight and high purity (Barns, 1994; Holben, 1994). If inhibitors are present, there are several protocols which utilize cell isolation which can be employed (Holben, 1994). Additionally, a fractionation technique, such as the bis-benzimide separation (cesium chloride isolation) described below, can be used to enhance the purity of the DNA.

Fractionation

Fractionation of the DNA samples prior to normalization increases the chances of cloning DNA from minor species from the pool of organisms sampled. In the present invention, DNA is preferably fractionated using a density centrifugation technique. One example of such a Technique is a cesium-chloride gradient. Preferably, the technique is performed in the presence of a nucleic acid intercalating agent which will bind regions of the DNA and cause a change in the buoyant density of the nucleic acid. More preferably, the nucleic acid intercalating agent is a dye, such as bis-benzimide which will preferentially bind regions of DNA (AT in the case of bis-benzimide) (Muller, 1975; Manuelidis, 1977). When nucleic acid complexed with an intercalating agent, such as bis-benzimide, is separated in an appropriate cesium-chloride gradient, the nucleic acid is fractionated. If the intercalating agent preferentially binds regions of the DNA, such as GC or AT regions, the nucleic acid is separated based on relative base content in the DNA. Nucleic acid from multiple organisms can be separated in this manner.

Density gradients are currently employed to fractionate nucleic acids. For example, the use of bis-benzimide density gradients for the separation of microbial nucleic acids for use in soil typing and bioremediation has been described. In these experiments, one evaluates the relative abundance of $A_{260}$ peaks within fixed benzimide gradients before and after remediation treatment to see how the bacterial populations have been affected. The technique relies on the premise that on the average, the GC content of a species is relatively consistent. This technique is applied in the present invention to fractionate complex mixtures of genomes. The nucleic acids derived from a sample are subjected to ultracentrifugation and fractionated while measuring the $A_{260}$ as in the published procedures.

In one aspect of the present invention, equal $A_{260}$ units are removed from each peak, the nucleic acid is amplified using a variety of amplification protocols known in the art, including those described hereafter, and gene libraries are prepared. Alternatively, equal $A_{260}$ units are removed from each peak, and gene libraries are prepared directly from this nucleic acid. Thus, gene libraries are prepared from a combination of equal amounts of DNA from each peak. This strategy enables access to genes from minority organisms within environmental samples and enrichments, whose genomes may not be represented or may even be lost, due to the fact that the organisms are present in such minor quantity, if a library was construed from the total unfractionated DNA sample. Alternatively, DNA can be normalized subsequent to fractionation, using techniques described hereafter. DNA libraries can then be generated from this fractionated/normalized DNA.

The composition of multiple fractions of the fractionated nucleic acid can be determined using PCR related amplification methods of classification well known in the art.

Normalization

Previous normalization protocols have been designed for constructing normalized cDNA libraries (WO 95/08647, WO 95/11986). These protocols were originally developed for the cloning and isolation of rare cDNA's derived from mRNA. The present invention relates to the generation of normalized genomic DNA gene libraries from uncultured or environmental samples.

Nucleic acid samples isolated directly from environmental samples or from primary enrichment cultures will typically contain genomes from a large number of microorganisms. These complex communities of organisms can be described by the absolute number of species present within a population and by the relative abundance of each organisms within the sample. Total normalization of each organisms within a sample is very difficult to achieve. Separation techniques such as optical tweezers can be used to pick morphologically distinct members with a sample. Cells from each member can then be combined in equal numbers or pure cultures of each member within a sample can be prepared and equal numbers of cells from each pure culture combined to achieve normalization. In practice, this is very difficult to perform, especially in a high thru-put manner.

The present invention involves the use of techniques to approach normalization of the genomes present within an environmental sample, generating a DNA library from the normalized nucleic acid, and screening the library for an activity of interest.

In one aspect of the present invention, DNA is isolated from the sample and fractionated. The strands of nucleic acid are then melted and allowed to selectively reanneal under fixed conditions ($C_o t$ driven hybridization). Alternatively, DNA is not fractionated prior to this melting process. When a mixture of nucleic acid fragments is melted and allowed to reanneal under stringent conditions, the common sequences find their complementary strands faster than the rare sequences. After an optional single-stranded nucleic acid isolation step, single-stranded nucleic acid, representing an enrichment of rare sequences, is amplified and used to generate gene libraries. This procedure leads to the amplification of rare or low abundance nucleic acid molecules. These molecules are then used to generate a library. While all DNA will be recovered, the identification of the organism originally containing the DNA may be lost. This method offers the ability to recover DNA from "unclonable sources."

Nucleic acid samples derived using the previously described technique are amplified to complete the normalization process. For example, samples can be amplified using PCR amplification protocols such as those described by Ko et al. (Ko, 1990b; Ko, 1990a, Takahashi, 1994), or more preferably, long PCR protocols such as those described by Barnes (1994) or Cheng (1994).

Normalization can be performed directly, or steps can also be taken to reduce the complexity of the nucleic acid pools prior to the normalization process. Such reduction in complexity can be beneficial in recovering nucleic acid from the poorly represented organisms.

The microorganisms from which the libraries may be prepared include prokaryotic microorganisms, such as Eubacteria and Archaebacteria, and lower eukaryotic microorganisms such as fungi, some algae and protozoa. The microorganisms may be cultured microorganisms or uncultured microorganisms obtained from environmental samples and such microorganisms may be extremophiles, such as thermophiles, hyperthermophiles, psychrophiles, psychrotrophs, etc.

As indicated above, the library may be produced from environmental samples in which case DNA may be recovered without culturing of an organism or the DNA may be recovered from a cultured organism.

Sources of microorganism DNA as a starting material library from which target DNA is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, genomic DNA may be recovered from either a culturable or non-culturable organism and employed to produce an appropriate recombinant expression library for subsequent determination of enzyme activity.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

It is important to further research gene clusters and the extent to which the full length of the cluster is necessary for the expression of the proteins resulting therefrom. Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides and post-polyketide biosynthesis genes for generation of novel polyketides for study is appealing. The method(s) of the present invention make it possible to and facilitate the cloning of novel polyketide synthases, since one can generate gene banks with clones containing large inserts (especially when using the f-factor based vectors), which facilitates cloning of gene clusters.

Preferably, the gene cluster DNA is ligated into a vector, particularly wherein a vector further comprises expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples.

Library Screening

After normalized libraries have been generated, unique enzymatic activities can be discovered using a variety of solid- or liquid-phase screening assays in a variety of formats, including a high-throughput robotic format described herein. The normalization of the DNA used to construct the libraries is a key component in the process. Normalization will increase the representation of DNA from important organisms, including those represented in minor amounts in the sample.

EXAMPLE 1

DNA Isolation

1. Samples are resuspended directly in the following buffer:
   500 mM Tris-HCl, pH 8.0
   100 mM NaCl
   1 mM sodium citrate
   100 µg/ml polyadenosine
   5 mg/ml lysozyme
2. Incubate at 37° C. for 1 hour with occasional agitation.
3. Digest with 2 mg/ml Proteinase K enzyme (Boehringer Mannheim) at 37° C. for 30 min.
4. Add 8 ml of lysis buffer [200 mM Tris-HCl, pH 8.0/100 mM NaCl/4% (wt/vol) SDS/10% (wt/vol) 4-aminosalicylate] and mix gently by inversion.
5. Perform three cycles of freezing in a dry ice-ethanol bath and thawing in a 65° C. water bath to release nucleic acids.
6. Extract the mixture with phenol and then phenol/chloroform/isoamyl alcohol.
7. Add 4 grams of acid-washed polyvinylpolypyrrolidone (PVPP) to the aqueous phase and incubate 30 minutes at 37° C. to remove organic contamination.
8. Pellet PVPP and filter the supernatant through a 0.45 µm membrane to remove residual PVPP.
9. Precipitate nucleic acids with isopropyl alcohol.
10. Resuspend pellet in 500 µl TE (10 mM Tris-HCl, pH 8.0/1.0 mM EDTA)
11. Add 0.1 g of ammonium acetate and centrifuge mixture at 4° C. for 30 minutes.
12. Precipitate nucleic acids with isopropanol.

EXAMPLE 2

Bis-Benzimide Separation of DNA

Sample composed of genomic DNA from *Clostridium perfringens* (27% G+C), *Escherichia coli* (49% G+C) and *Micrococcus lysodictium* (72% G+C) was purified on a cesium-chloride gradient. The cesium chloride (Rf=1.3980) solution was filtered through a 0.2 µm filter and 15 ml were loaded into a 35 ml OptiSeal tube (Beckman). The DNA was added and thoroughly mixed. Ten micrograms of bis-benzimide (Sigma; Hoechst 33258) were added and mixed thoroughly. The tube was then filled with the filtered cesium chloride solution and spun in a VTi50 rotor in a Beckman L8-70 Ultracentrifuge at 33,000 rpm for 72 hours. Following centrifugation, a syringe pump and fractionator (Brandel Model 186) were used to drive the gradient through an ISCO UA-5 UV absorbance detector set to 280 nm. Three peaks representing the DNA from the three organisms were obtained. PCR amplification of DNA encoding rRNA from a 10-fold dilution of the *E. coli* peak was performed with the following primers to amplify eubacterial sequences:

Forward primer: (27F)
5'-AGAGTTTGATCCTGGCTCAG-3' (SEQ ID NO:1)
Reverse primer: (1492R)
5'-GGTTACCTTGTTACGACTT-3' (SEQ ID NO:2)

EXAMPLE 3

Sample of DNA Obtained from the Gill Tissue of a Clam Harboring an Endosymbiont which Cannot be Physically Separated from its Host Purify DNA on cesium chloride gradient according to published protocols (Sambrook, 1989).
2. Prepare second cesium chloride solution; (Rf=1.3980) filter through 0.2 µm filter and load 15 ml into a 35 ml OptiSeal tube (Beckman).

3. Add 10 μg bis-benzimide (Sigma; Hoechst 33258) and mix.
4. Add 50 μg purified DNA and mix thoroughly.
5. Spin in a VTi50 rotor in a Beckman L8-70 Ultracentrifuge at 33,000 rpm for 72 hours.
6. Use syringe pump and fractionator (Brandel Model 186) to drive gradient through an ISCO UA-5 UV absorbance detector set to 280 nm.

EXAMPLE 4

Complexity Analysis 1. 16S rRNA analysis is used to analyze the complexity of the DNA recovered from environmental samples (Reysenbach, 1992; DeLong, 1992; Barns, 1994) according to the protocol outlined in Example 1.
2. Eubacterial sequences are amplified using the following primers:
Forward:
5'-AGAGTTTGATCCTGGCTCAG-3' (SEQ ID NO:3)
Reverse:
5'-GGTTACCTTGTTACGACTT-3' (SEQ ID NO:4)
Archaeal sequences are amplified using the following primers:
Forward:
5'GCGGATCCGCGGCCGCTGCACAYCTGGT YGATYCTGCC-3' (SEQ ID NO:5)
Reverse:
5'-GACGGGCGGTGTGTRCA-3' (SEQ ID NO:6)
(R=purine,; Y-pyrimidine)
3. Amplification reactions proceed as published. The reaction buffer used in the amplification of the archaeal sequences includes 5% acetamide (Barns, 1994).
4. The products of the amplification reactions are rendered blunt ended by incubation with Pfu DNA polymerase.
5. Blunt end ligation into the pCR-Script plasmid in the presence of SrfI restriction endonuclease according to the manufacturer's protocol (Strategene Cloning Systems).
6. Samples are sequenced using standard sequencing protocols (reference) and the number of different sequences present in the sample is determined.

EXAMPLE 5

Normalization

Purified DNA is fractionated according to the bis-benzimide protocol of Example (2), and recovered DNA is sheared or enzymatically digested to 3–6 kb fragments. Lone-linker primers are ligated and the DNA is sized selected. Size-selected DNA is amplified by PCR, if necessary.

Normalization is then accomplished as follows:

1. Double-stranded DNA sample is resuspended in hybridization buffer (0.12 M $NaH_2PO_4$, pH 6.8/0.82 M NaCl/1 mM EDTA/0.1% SDS).
2. Sample is overlaid with mineral oil and denatured by boiling for 10 minutes.
3. Sample is incubated at 68° C. for 12–36 hours.
4. Double-stranded DNA is separated from single-stranded DNA according to standard protocols (Sambrook, 1989) on hydroxyapatite at 60° C.
5. The single-stranded DNA fraction is desalted and amplified by PCR.
6. The process is repeated for several more rounds (up to 5 or more).

EXAMPLE 6

Library Construction

1. Genomic DNA dissolved in TE buffer is vigorously passed through a 25 gauge double-hubbed needle until the sheared fragments are in the desired size range.
2. DNA ends are "polished" or blunted with Mung Bean nuclease.
3. EcoRI restriction sites in the target DNA are protected with EcoRI methylase.
4. EcoRI linkers [GGAATTCC (SEQ ID NO:7)] are ligated to the blunted/protected DNA using a very high molar ratio of linkers to target DNA.
5. Linkers are cut back with EcoRI restriction endonuclease and the DNA is size fractionated using sucrose gradients.
6. Target DNA is ligated to the λZAPII vector, packaged using in vitro lambda packing extracts, and grown in the appropriate *E. coli* XLI Blue host cell.

EXAMPLE 7

Library Screening

The following is a representative example of a procedure for screening an expression library prepared in accordance with Example 6.

The general procedures for testing for various chemical characteristics is generally applicable to substrates other than those specifically referred to in this Example.

Screening for Activity. Plates of the library prepared as described in Example 6 are used to multiply inoculate a single plate containing 200 μL of LB Amp/Meth, glycerol in each well. This step is performed using the High Density Replicating Tool (HDRT) of the Beckman Biomek with a 1% bleach, water, isopropanol, air-dry sterilization cycle between each inoculation. The single plate is grown for 2 h at 37° C. and is then used to inoculate two white 96-well Dynatech microtiter daughter plates containing 250 μL of LB Amp/Meth, glycerol in each well. The original single plate is incubated at 37° C. for 18 h, then stored at −80° C. The two condensed daughter plates are incubated at 37° C. also for 18 h. The condensed daughter plates are then heated at 70° C. for 45 min. to kill the cells and inactivate the host *E.coli* enzymes. A stock solution of 5 mg/mL morphourea phenylalanyl-7-amino-4-trifluoromethyl coumarin (MuPheAFC, the 'substrate') in DMSO is diluted to 600 μM with 50 mM pH 7.5 Hepes buffer containing 0.6 mg/mL of the detergent dodecyl maltoside.

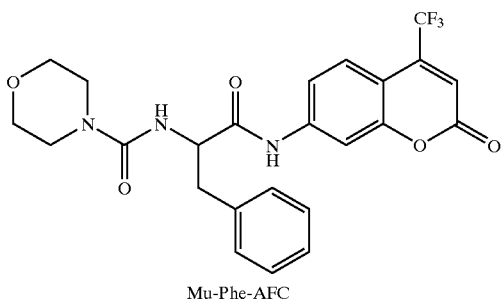

Mu-Phe-AFC

Fifty μL of the 600 μM MuPheAFC solution is added to each of the wells of the white condensed plates with one 100 μL mix cycle using the Biomek to yield a final concentration of substrate of ~100 μM. The fluorescence values are recorded (excitation=400 nm, emission=505 nm) on a plate reading fluorometer immediately after addition of the substrate (t=0). The plate is incubated at 70° C. for 100 min, then allowed to cool to ambient temperature for 15 additional minutes. The fluorescence values are recorded again (t=100). The values at t=0 are subtracted from the values at t=100 to determine if an active clone is present.

The data will indicate whether one of the clones in a particular well is hydrolyzing the substrate. In order to determine the individual clone which carries the activity the source library plates are thawed and the individual clones are used to singly inoculate a new plate containing LB Amp/Meth, glycerol. As above, the plate is incubated at 37° C. to grow the cells, heated at 70° C. to inactivate the host enzymes, and 50 μL of 600 μM MuPheAFC is added using the Biomek. Additionally three other substrates are tested. They are methyl umbelliferone heptanoate. the CBZ-arginine rhodamine derivative, and fluorescein-conjugated casein (~3.2 mol fluorescein per mol of casein).

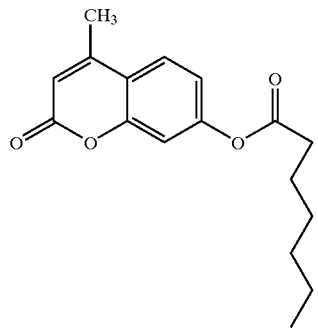

methyl umbelliferone heptanoate

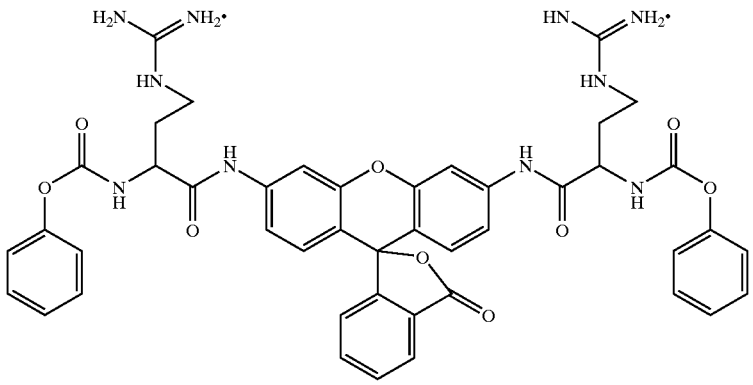

(CBZ-arginine)$_2$ rhodamine 110

The umbelliferone and rhodamine are added as 600 μM stock solutions in 50 μL of Hepes buffer. The fluorescein conjugated casein is also added in 50 μL at a stock concentration of 20 and 200 mg/mL. After addition of the substrates the t=0 fluorescence values are recorded, the plate is incubated at 70° C., and the t=100 min. values are recorded as above.

These data indicate which plate the active clone is in, where the arginine rhodamine derivative is also turned over by this activity, but the lipase substrate, methyl umbelliferone heptanoate, and protein, fluorescein-conjugated casein, do not function as substrates.

Chiral amino esters may be determined using at least the following substrates:

Chiral amino esters may be determined using at least the following substrates:

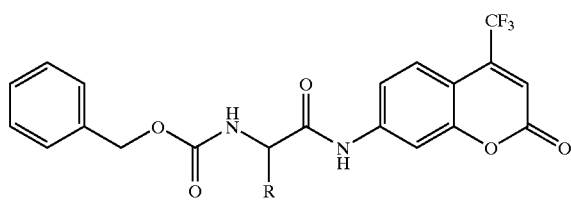

R = CH₃
CH₂-OH
CH₂-CO₂⁻

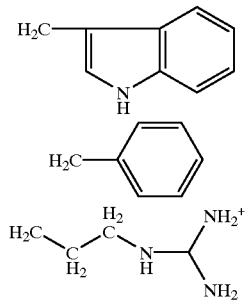

For each substrate which is turned over the enantioselectivity value, E, is determined according to the equation below:

$$E = \frac{\ln[(1 - c(1 + ee_p)]}{\ln[(1 - c(1 - ee_p)]}$$

where $ee_p$=the enantiomeric excess (ee) of the hydrolyzed product and c=the percent conversion of the reaction. See Wong and Whitesides, Enzymes in Synthetic Organic Chemistry, 1994, Elsevier, Tarrytown, N.Y., pp. 9–12.

The enantiomeric excess is determined by either chiral high performance liquid chromatography (HPLC) or chiral capillary electrophoresis (CE). Assays are performed as follows: two hundred μL of the appropriate buffer is added to each well of a 96-well white microtiter plate, followed by 50 μL of partially or completely purified enzyme solution; 50 μL of substrate is added and the increase in fluorescence monitored versus time until 50% of the substrate is consumed or the reaction stops, whichever comes first.

EXAMPLE 8

Construction of a Stable, Large Insert Picoplankton Genomic DNA Library

Cell collection and preparation of DNA. Agarose plugs containing concentrated picoplankton cells were prepared from samples collected on an oceanographic cruise from Newport, Oreg. to Honolulu, Hi. Seawater (30 liters) was collected in Niskin bottles, screened through 10 μm Nitex, and concentrated by hollow fiber filtration (Amicon DC10) through 30,000 MW cutoff polyfulfone filters. The concentrated bacterioplankton cells were collected on a 0.22 μm, 47 mm Durapore filter, and resuspended in 1 ml of 2×STE buffer (1M NaCl, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCl, 0.1M EDTA, 1% Sarkosyl, 0.2% sodium deoxycholate, 1 mg/ml lysozyme) and incubated at 37° C. for one hour. The agarose plug was then transferred to 40 mls of ESP Buffer (1% Sarkosyl, 1 mg/ml proteinase K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 μl) prepared from a sample collected off the Oregon coast was dialyzed overnight at 4° C. against 1 mL of buffer A (100 mM NaCl, 10 mM Bis Tris Propane-HCl, 100 μg/ml acetylated BSA: pH 7.0 @25° C.) in a 2 mL microcentrifuge tube. The solution was replaced with 250 μl of fresh buffer A containing 10 mM MgCl₂ and 1 mM DTT and incubated on a rocking platform for 1 hr at room temperature. The solution was then changed to 250 μl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the enzyme and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile H₂O to a concentration of 2.5 ng/μl for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., high abundance of Archaea in Antarctic marine picoplankton, *Nature,* 371:695–698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately 7.5×10$^5$ cells, therefore approximately 5.4×10 cells were present in the 72 μl slice used in the preparation of the partially digested DNA.

Vector arms were prepared from pFOS1 as described (Kim et al., Stable propagation of casmid sized human DNA inserts in an F factor based vector, *Nucl. Acids Res.*, 20:10832–10835, 1992). Briefly, the plasmid was completely digested with AstlI, dephosphorylated with HK phosphatase, and then digested with BamHI to generate two arms, each of which contained a cos site in the proper orientation for cloning and packaging ligated DNA between 35–45 kbp. The partially digested picoplankton DNA was ligated overnight to the PFOS1 arms in a 15 μl ligation reaction containing 25 ng each of vector and insert and 1U of T4 DNA ligase (Boehringer-Mannheim). The ligated DNA in four microliters of this reaction was in vitro packaged using the Gigapack XL packaging system (Stratagene), the fosmid particles transfected to *E. coli* strain DH10B (BRL), and the cells spread onto LB$_{cm15}$ plates. The resultant fosmid clones were picked into 96-well microliter dishes containing LB$_{cm15}$ supplemented with 7% glycerol. Recombinant fosmids, each containing ca. 40 kb of picoplankton DNA insert, yielded a library of 3.552 fosmid clones, containing approximately 1.4×10$^8$ base pairs of cloned DNA. All of the clones examined contained inserts ranging from 38 to 42 kbp. This library was stored frozen at −80° C. for later analysis.

Numerous modifications and variations of the present invention are possible in light of the above teachings; therefore, within the scope of the claims, the invention may be practiced other than as particularly described.

LITERATURE CITED

Amann, R. I., Ludwig, W. and Schleifer, K-H (1995) *Microbiological Reviews*, 59:143–169
Barnes, W. M. (1994) *Proceedings of the National Academy of Sciences, USA*, 91:2216–2220
Barns, S. M., Fundyga, R. E., Jeffries, M. W. and Pace, N. R. (1994) *Proceedings of the National Academy of Sciences, USA*, 91:1609–1613
Chan, M. K., Mukund, S., Kletzin, A., Adams, M. W. W. and Rees, D. C. (1995) *Science*, 267:1463–1469
Cheng, S., Fockler, C., Barnes, W. and Higuchi, R. (1994) *Proceedings of the National Academy of Sciences, USA* 91:5695–5699
Cline, J., Braman, J. and Kretz, K. (1995) Strategies in Molecular Biology (in press)
Danson, M. J. (1989) *Canadian Journal of Microbiology*, 35:58–64
DeLong, E. F. (1992) *Proceedings of the National Academy of Sciences, USA*, 89:5685–5689
Enzyme Nomenclature, Academic Press: NY, 1992
Giovannoni, S. J., Britschgi, T. B., Moyer, C. L. and Field, K. G. (1990) *Nature*, 345:60–63
Holben, W. E. (1994) Methods of Soil Analysis, Part 2, Microbiological and Biochemical Properties 727–751
Holben, W. E. and Harris D. (1995) Molecular Ecology, 4(5):627–31
Ko, M. S. H. (1990a) *Nucleic Acids Research*, 18:5705–5711
Ko, M. S. H., Ko, S. B. H., Takahashi, N., Nishiguchi, K. and Abe, K. (1990b) *Nucleic Acids Research*, 18:4293–4294
Lundberg, K. S., Shoemaker, D. D., Adams, M. W. W., Short, J. M., Sorge, J. A. and Mathur, E. J. (1991) *Gene*, 108:1–6
Manuelidis, L. (1977) *Analytical Biochemistry*, 78:561–568
Muller, W. and Gautier, F. (1975) *European Journal of Biochemistry*, 54:385–394
Nielson, K., Scott, B. and Kretz, K. (1994) *Strategies in Molecular Biology*, 7:64–65
Reysenbach, A-L., Giver, L. J., Wickham, G. S. and Pace, N. R. (1992) *Applied and Environmental Microbiology*, 58:3417–3418
Saiki, R. K., Gelfand, D. H., Stoffel, S., Scharf, S. J., Higuchi, R., Horn, G. T., Mullis, K. B. and Erlich, H. A. (1988) *Science*, 239:487–491
Sambrook, J., Fritsch, E. F. and Maniatis, T. (1989) Molecular Cloning: A Laboratory Manual, Cold Spring Habor Press, Cold Spring Habor, N.Y.
Short, J. M. and Sorge, J. A. (1991) *Methods in Enzymology*, 216:495–516
Short, J. M., Fernandez, J. M., Sorge, J. A. and Huse, W. D. (1988) *Nucleic Acids Research*, 16:7583–7600
Smith, C. R., Kukert, H., Wheatcroft, R. A., Jumars, P. A. and Deming, J. W. (1989) *Nature*, 341:27–28
Starnes, et al. (1990) Presented at the 5th International Symposium on Cyclodextrins, Paris, France
Takahashi, N. and Ko, M. S. H. (1994) *Genomics*, 23:202–210
Torsvik, V., Goksoyr, J. and Daae, F. L. (1990a) *Applied and Environmental Microbiology*, 56:782–787
Torsvik, V., Salte, K., Sorheim, R. and Goksoyr, J. (1990b) *Applied and Environmental Microbiology*, 56:776–781
Trotter, P. C. (1990) *Tappi Journal*, 73:198–204
Ward, D. M., Weller, R. and Bateson, M. M. (1990) *Nature*, 345:63–65
Zamost, B. L., Brantley, Q. I., Elm, D. D. and Beck, C. M. (1990) *Journal of Industrial Microbiology*, 5:303–312
Zamost, B. L., Nielson, H. K. and Starnes, R. L. (1991) *Journal of Industrial Microbiology*, 8:71–81

TABLE 1

A2

Fluorescein conjugated casein (3.2 mol fluorescein/mol casein)
CBZ-Ala-AMC
t-BOC-Ala-Ala-Asp-AMC
succinyl-Ala-Gly-Leu-AMC
CBZ-Arg-AMC
CBZ-Met-AMC
morphourea-Phe-AMC
t-BOC = t-butoxy carbonyl, CBZ = carbonyl benzyloxy.
AMC = 7-amino-4-methyl coumarin

AA3

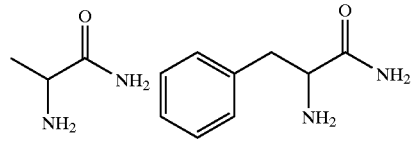

AB3

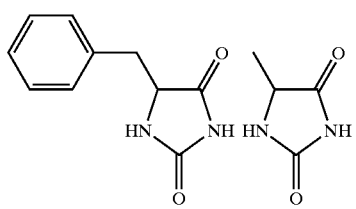

TABLE 1-continued

AC3

[Chemical structures of N-acetyl-alanine and N-acetyl-phenylalanine]

AD3

Fluorescein conjugated casein
t-BOC-Ala-Ala-Asp-AFC
CBZ-Ala-Ala-Lys-AFC
succinyl-Ala-Ala-Phe-AFC
succinyl-Ala-Gly-Leu-AFC
AFC = 7-amino-4-trifluoromethyl coumarin.)

AE3

Flourescein conjugated casein

AF3 t-BOC-Ala-Ala-Asp-AFC
CBZ-Asp-AFC

AG3

CBZ-Ala-Ala-Lys-AFC
CBZ-Arg-AFC

AH3 succinyl-Ala-Ala-Phe-AFC
CBZ-Phe-AFC
CBZ-Trp-AFC

AI3 succinyl-Ala-Gly-Leu-AFC
CBZ-Ala-AFC
CBZ-Sewr-AFC

TABLE 2

L2

[Chemical structures of 4-methylumbelliferyl esters with various alkyl chain lengths]

TABLE 2-continued

[Additional chemical structures of 4-methylumbelliferyl esters including short chain (propionate), long chain saturated, and unsaturated fatty acid esters]

LA3

TABLE 2-continued
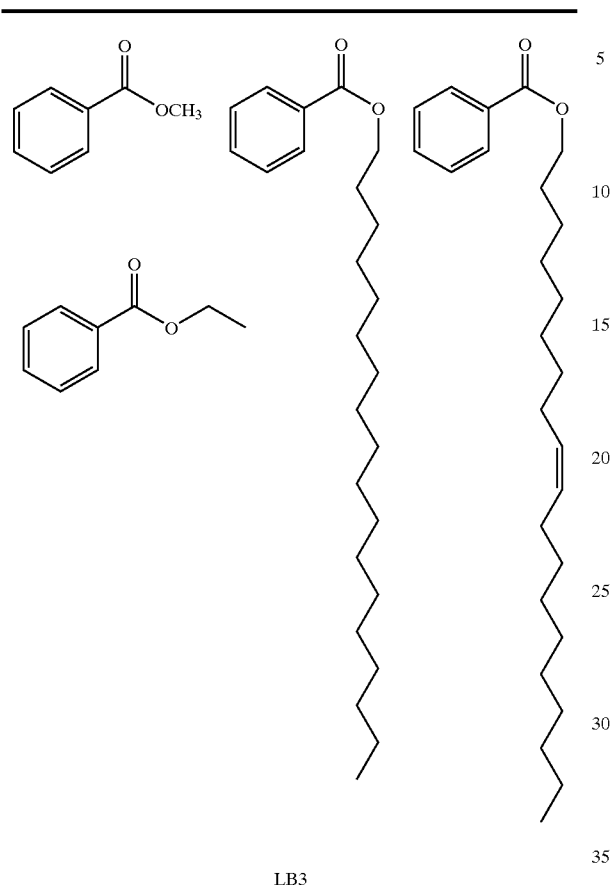
LB3
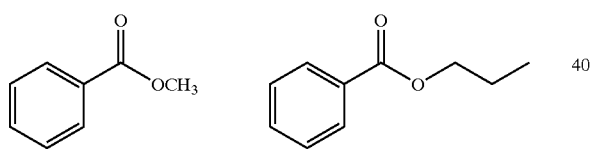
LC3
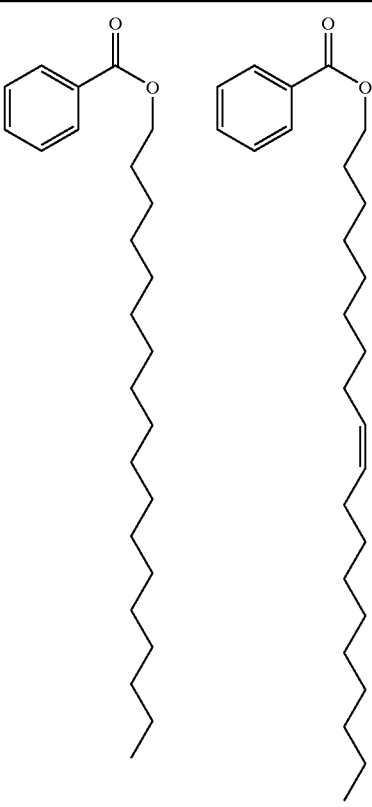
LD3
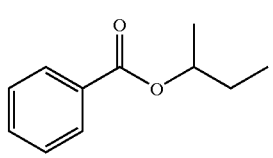
LE3
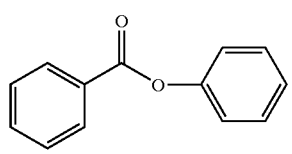
And all of L2
LF3
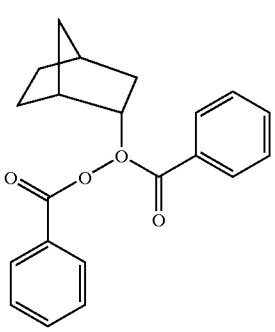
LG3

TABLE 2-continued
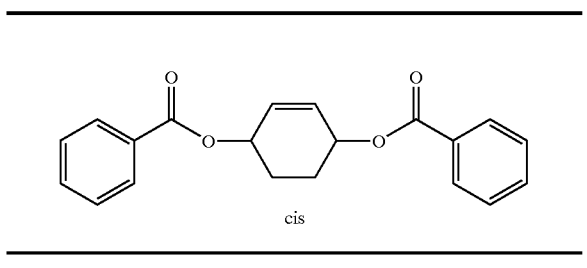
cis
TABLE 3
LH3
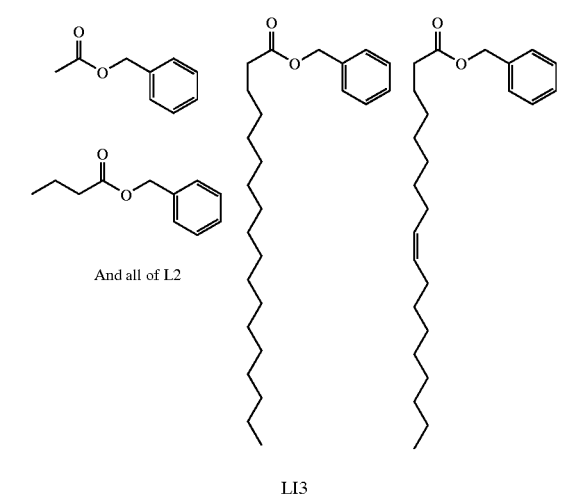
And all of L2
LI3
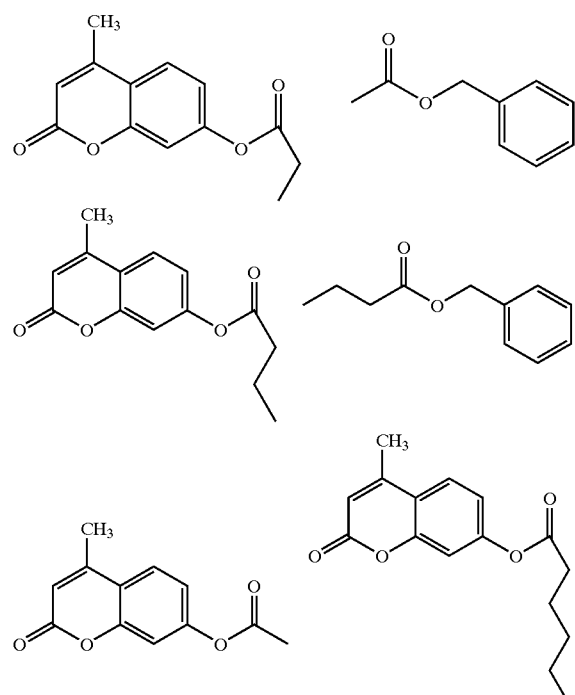
LJ3
TABLE 3-continued
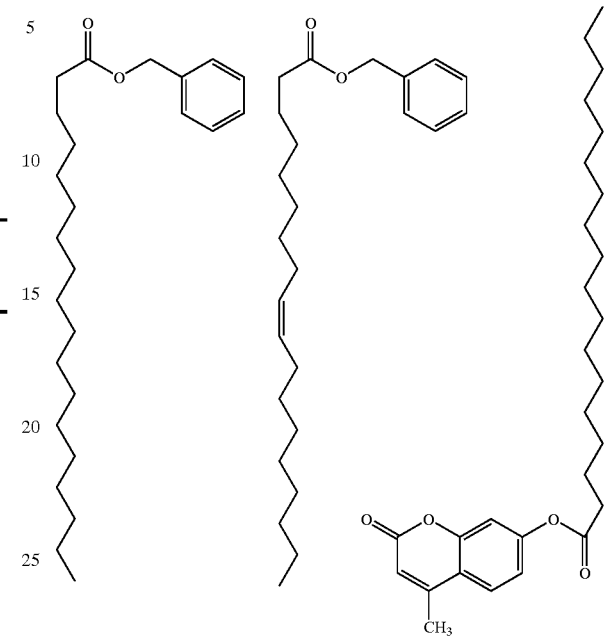
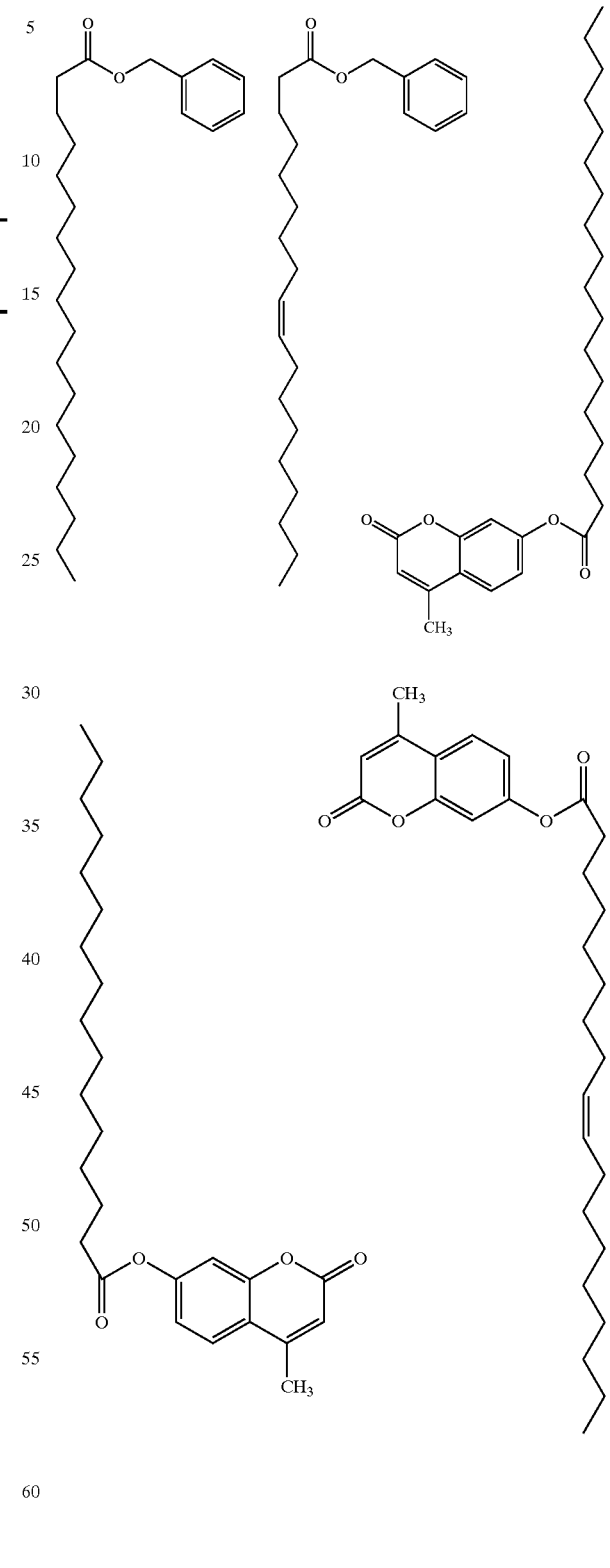

TABLE 3-continued

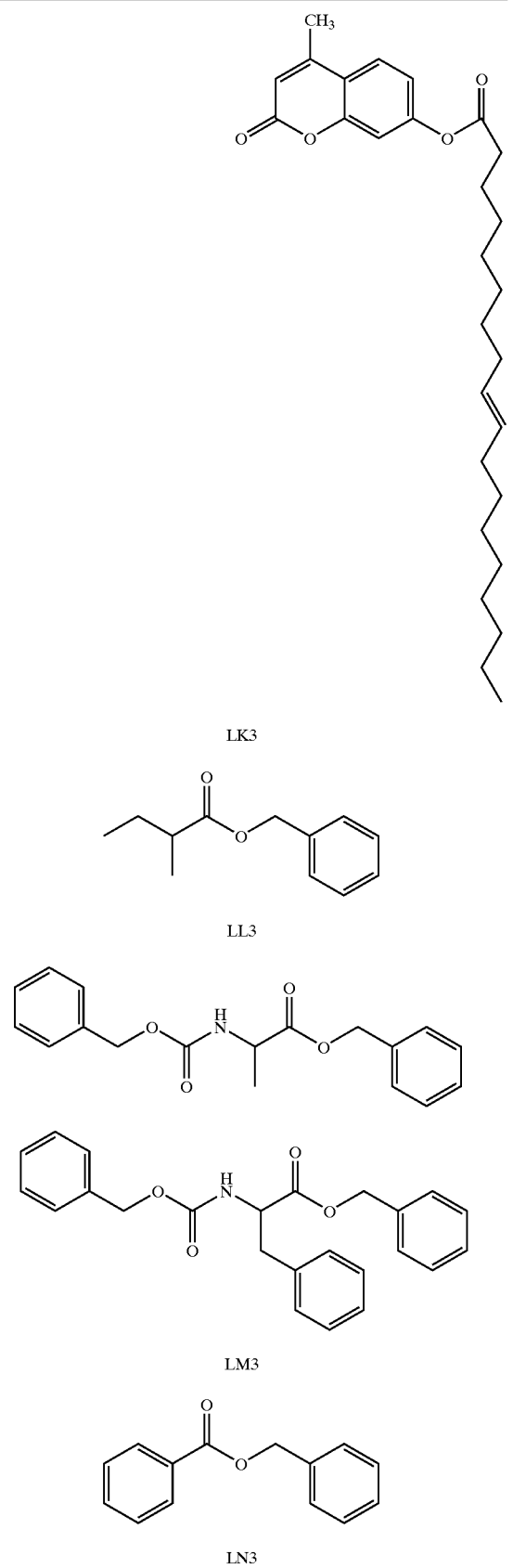

TABLE 3-continued

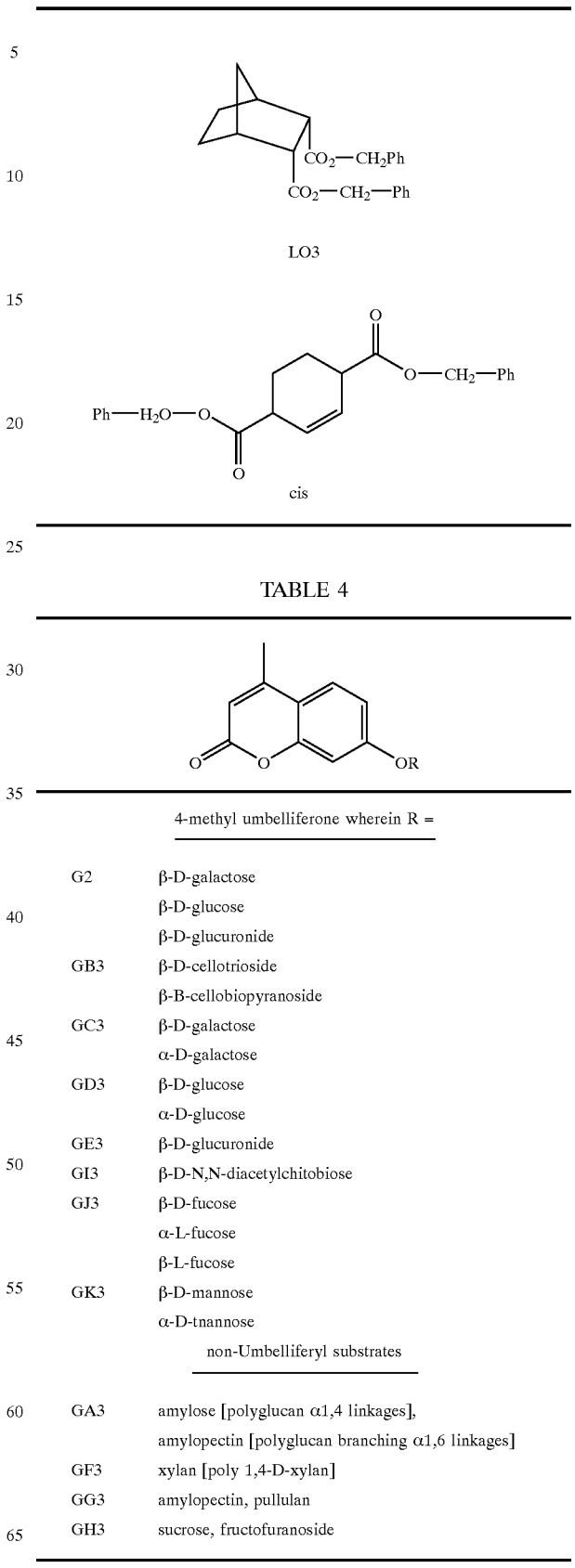

TABLE 4

| | 4-methyl umbelliferone wherein R = |
|---|---|
| G2 | β-D-galactose |
| | β-D-glucose |
| | β-D-glucuronide |
| GB3 | β-D-cellotrioside |
| | β-B-cellobiopyranoside |
| GC3 | β-D-galactose |
| | α-D-galactose |
| GD3 | β-D-glucose |
| | α-D-glucose |
| GE3 | β-D-glucuronide |
| GI3 | β-D-N,N-diacetylchitobiose |
| GJ3 | β-D-fucose |
| | α-L-fucose |
| | β-L-fucose |
| GK3 | β-D-mannose |
| | α-D-tnannose |
| | non-Umbelliferyl substrates |
| GA3 | amylose [polyglucan α1,4 linkages], |
| | amylopectin [polyglucan branching α1,6 linkages] |
| GF3 | xylan [poly 1,4-D-xylan] |
| GG3 | amylopectin, pullulan |
| GH3 | sucrose, fructofuranoside |

What is claimed is:

1. A method for forming a normalized DNA library from a mixed population of organisms, which comprises:
   (a) obtaining a DNA population from the mixed population of organisms;
   (b) at least one of the steps selected from the group consisting of (i) amplifying the copy number of the DNA population so isolated and (ii) recovering a fraction of the isolated DNA having a desired characteristic; and
   (c) normalizing the representation of various DNAs within the DNA population so as to form a normalized library of DNA from the mixed population of organisms.

2. The method of claim 1, further comprising prior to (b) fractionating the DNA population by contacting the DNA population with an intercalating agent and separating the DNA.

3. The method of claim 2, wherein the intercalating agent is bis-benzimide.

4. The method of claim 1, which comprises recovering a fraction of the isolated DNA having a desired characteristic.

5. The method of claim 1, which comprises amplifying the copy number of the DNA population so isolated.

6. The method of claim 1, wherein the amplifying the DNA precedes normalizing.

7. The method of claim 1, wherein normalizing the DNA precedes amplifying.

8. The method of claim 1, which comprises both the steps of (i) amplifying the copy number of the DNA population so isolated and (ii) recovering a fraction of the isolated DNA having a desired characteristic.

9. A normalized DNA library formed from a mixed population of organisms by a method comprising:
   (a) obtaining a DNA population from the mixed population of organisms;
   (b) at least one of (i) amplifying the copy number of the DNA population so isolated and (ii) recovering a fraction of the isolated DNA having a desired characteristic;
   (c) normalizing the representation of various DNAs within the DNA population; and
   (d) transforming host cells with the DNA of (c) so as to form a normalized library of DNA from the mixed population of organisms.

10. The library of claim 9, further comprising prior to (b) fractionating the DNA population by contacting the DNA population with an intercalating agent and separating the DNA.

11. The library of claim 10, wherein the intercalating agent is bis-benzimide.

12. The library of claim 9, wherein the method of forming said library comprises recovering a fraction of the isolated DNA having a desired characteristic.

13. The library of claim 9, wherein the method of forming said library comprises amplifying the copy number of the DNA population so isolated.

14. The library of claim 9, wherein in the method of forming said library amplifying the DNA precedes normalizing.

15. The library of claim 9, wherein in the method of forming said library normalizing the DNA precedes amplifying.

16. The library of claim 9, wherein the method of forming said library comprises both the steps of (i) amplifying the copy number of the DNA population so isolated and (ii) recovering a fraction of the isolated DNA having a desired characteristic.

17. A method for producing a normalized library of gene clusters from a mixed population of organisms, which comprises:
   (a) obtaining a DNA population from the mixed population of organisms;
   (b) at least one of (i) amplifying the copy number of the DNA population so isolated and (ii) recovering a fraction of the isolated DNA having a desired characteristic; and
   (c) normalizing the representation of various DNAs within the DNA population so as to produce a normalized library of DNA from the mixed population of organisms.

18. The method of claim 17, further comprising prior to (b) fractionating the DNA population by contacting the DNA population with an intercalating agent and separating the DNA.

19. A normalized library of gene clusters formed from a mixed population of organisms by a method comprising:
   (a) obtaining a DNA population from the mixed population of organisms;
   (b) at least one of (i) amplifying the copy number of the DNA population so isolated and (ii) recovering a fraction of the isolated DNA having a desired characteristic; and
   (c) normalizing the representation of various DNAs within the DNA population so as to form a normalized library of DNA from the mixed population of organisms.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

AGAGTTTGAT CCTGGCTCAG                                          20

(2) INFORMATION FOR SEQ ID NO:2:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

GGTTACCTTG TTACGACTT                                           19

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

AGAGTTTGAT CCTGGCTCAG                                          20

(2) INFORMATION FOR SEQ ID NO:4:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

GGTTACCTTG TTACGACTT                                           19

(2) INFORMATION FOR SEQ ID NO:5:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (genomic)

(xi) FEATURE:

-continued

```
        (D) OTHER INFORMATION:  Y=pyrimidine (xi) SEQUENCE DESCRIPTION: SEQ ID NO:5:

GCGGATCCGC GGCCGCTGCA CAYCTGGTYG ATYCTGCC                          38

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) FEATURE:
        (D) OTHER INFORMATION:  R=Purine (xi) SEQUENCE DESCRIPTION: SEQ ID NO:6:

GACGGGCGGT GTGTRCA                                                 17

(2) INFORMATION FOR SEQ ID NO:7:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGAATTCC                                                            8
```